United States Patent
Wasserman

(10) Patent No.: US 6,627,863 B2
(45) Date of Patent: Sep. 30, 2003

(54) SYSTEM AND METHODS TO DETERMINE THE SETTINGS OF MULTIPLE LIGHT SOURCES IN A VISION SYSTEM

(75) Inventor: Richard M. Wasserman, Redmond, WA (US)

(73) Assignee: Mitutoyo Corporation, Kawasaki (JP)

( * ) Notice: Subject to any disclaimer, the term of this patent is extended or adjusted under 35 U.S.C. 154(b) by 0 days.

(21) Appl. No.: 09/736,187

(22) Filed: Dec. 15, 2000

(65) Prior Publication Data

US 2002/0074480 A1 Jun. 20, 2002

(51) Int. Cl.$^7$ .................................................. G01J 1/32
(52) U.S. Cl. .................. 250/205; 250/559.39; 315/158; 382/152
(58) Field of Search .............................. 250/205, 214 R, 250/552, 553, 559.04, 559.07, 559.08, 559.39, 559.46, 208.1; 348/86–92, 125–134; 356/240.1, 237.4, 237.5, 394; 382/141, 145, 147, 152; 315/151, 158

(56) References Cited

U.S. PATENT DOCUMENTS

| | | | |
|---|---|---|---|
| 5,519,496 A | * | 5/1996 | Borgert et al. ............... 348/126 |
| 5,753,903 A | * | 5/1998 | Mahaney ..................... 250/205 |
| 6,207,946 B1 | * | 3/2001 | Jusoh et al. ............. 250/208.1 |
| 6,303,916 B1 | * | 10/2001 | Gladnick .................... 250/205 |

OTHER PUBLICATIONS

Leon, F. Puente, Enhanced Imaging by Fusion of Illumination Series, Jun. 20, 1997, p. 1–12.

* cited by examiner

Primary Examiner—Kevin Pyo
(74) Attorney, Agent, or Firm—Oliff & Berridge, PLC

(57) ABSTRACT

Image simulation system and method simulate an image based on a number of base images and a current lighting vector. An actual object to be viewed using the vision system is placed within the overall field of view of the vision system. Depending on the desired analysis to be made, either the entire object, or a specific portion of the object, is illuminated using one of the various illumination sources of the vision system. The base images of the objects, or of the particular portion of the object, are captured, where each base image is illuminated using a different illumination intensity of that single illumination source. This is repeated for each of the different illumination sources provided in the vision system. The simulated image is generated by combining various ones of the base images based on the light intensities of the lighting services defined in the current lighting vector. The simulated image can be evaluated to determine if it has a desired image quality. The lighting vector can be modified until a simulated image having the desired image quality is obtained. That lighting vector can then be used to obtain an actual image of the object that will have the desired image quality.

30 Claims, 7 Drawing Sheets

US 6,627,863 B2

SYSTEM AND METHODS TO DETERMINE THE SETTINGS OF MULTIPLE LIGHT SOURCES IN A VISION SYSTEM

BACKGROUND OF THE INVENTION

1. Field of Invention

This invention relates to lighting systems for vision systems.

2. Description of Related Art

The light output of any device is a function of many variables. Some of the variables include the instantaneous driving current, the age of the device, the ambient temperature, whether there is any dirt or residue on the light source, the performance history of the device, etc. Machine vision instrument systems typically analyze features or objects within their field of view using methods which may determine, among other things, the contrast within the region of interest where the features or objects may be found. To some degree, this determination is affected by the character of incident light or transmitted light.

A machine vision system programmer or operator often wishes to illuminate a workpiece so as to achieve a specific image characteristic. The image characteristic may be a specific average gray level value in a region of interest or a goal such as to maximize the difference in average gray level between various regions of interest, or to maximize a gradient within a region of interest. More generally, the desired characteristic may be a complex series of goals defined across an image scan line.

In many applications, the relationship between the imaging subsystem and the workpiece under inspection is predictable. In such applications, the predictability of the situation allows a simple form of reproducible lighting control. As illustrated in U.S. Pat. No. 5,753,903 to Mahaney, for example, closed-loop control systems are used to ensure that the output light intensity of a light source of a machine vision system was driven to a particular command level. These conventional closed-loop control systems prevent the output light intensity from drifting from the desired output light intensity due to variations in the instantaneous drive current, the age of the light source, the ambient temperature, or the like. Accordingly, it is possible to determine a level for a single, spatially fixed illumination source and an actual workpiece.

However, even when such a simple form of reproducible lighting control is possible, performing a search for an optimal light source setting can become problematic because each of the steps of light adjustment, acquisition of each video frame, and evaluation of each video frame, requires a finite period of time. In particular, common halogen lights require a period of time to stabilize their output after their current drive is altered. Thus, although there are several conventional approaches to choose a satisfactory light for a given workpiece and a single fixed light source, there may be some associated delays which reduce the available throughput of the associated vision system.

Methods are also known for creating macroscopic synthetic images through so-called "image fusion" of an illumination series. These methods generally deal with cases where different sub-regions of an object cannot simultaneously be adequately illuminated, yet it is desirable to combine the different sub-regions into a single macroscopic image of a region of interest that is everywhere adequately illuminated. Such macroscopic images can give an enhanced qualitative view of an object. In such methods, an illumination source is systematically varied. A series of images of the region of interest are acquired. Then, for each sub-region, the "best" images from the series are determined, "fused", and combined into a macroscopic synthetic image that is presumably everywhere well-illuminated.

It is noteworthy that, in such methods, selecting the illumination settings for each of image the illumination series is considered problematic.

Thus, an exhaustive, systematic variation of hardware lighting settings and image acquisition is performed to ensure that at least one acceptable image of each sub-region is obtained. Such a systematic variation is little more than a conventional trial and error approach, which is time consuming and inappropriate for many types of vision system operations where higher throughput is beneficial.

Furthermore, this method is not well-suited to achieve the most desirable image of any particular sub-region, since one of a reasonable number of brute-force systematic variations is unlikely to precisely coincide with the most desirable illumination settings for any particular sub-region. This is particularly unlikely if a number of different light sources are considered. Yet, for many machine vision applications, achieving the most desirable settings for a particular sub-region is the most important consideration.

Additionally, the complicated "fusion" process may produce unexpected results in the synthetic image. These unexpected results are generally not acceptable for applications requiring precise quantitative analysis of features on an object.

SUMMARY OF THE INVENTION

Thus, considering the problems of throughput, quantitative accuracy in the final image, and the ability to adapt to a variety of unpredictable workpiece features and configurations, conventional methods do not offer a reasonable solution for determining the most desirable illumination setting for a region of interest. This is particularly true when using multiple illumination sources. This problem is particularly significant in the design of a fully automated off-line part program generation system.

Thus, there is a need for a method for precisely acquiring an image regardless of the overhead, or time consumption, involved, and that achieves the desired image characteristics. Such a process could implement the use of a standard or novel search technique to search the problem landscape for the desired illumination setting, that is, the lighting settings for each of the various lighting sources. Currently, the main problem associated with conducting a trial and error search for a desirable combination of multiple light source settings is the overhead associated with changing the output power of each lamp and waiting for the trial images to be acquired and evaluated.

This invention provides systems and methods that allow a vision system to search for a desirable combination of multiple light source settings in a relatively short time.

This invention separately provides systems and methods that allow a vision system to identify a most desirable combination of multiple light source settings for any of a variety of feature analyses that are reliable, robust, and readily adaptable.

This invention separately provides systems and methods that simulate the effects of combinations of multiple light sources on an object to be viewed.

This invention further provides systems and methods that simulate the effects of multiple light sources on the object by sampling the actual effects of individual light sources on a number of intensity levels on the object.

This invention further provides systems and methods that sample intensities for single light sources and combine the interpolated results.

This invention further provides systems and methods that allow simulations of actual lighting effects of multiple lighting sources on an object to be generated based on discretely sampled intensity levels of each of the multiple light sources.

This invention further provides systems and methods that allow simulations of actual lighting effects of multiple lighting sources on an object to be generated based on relatively few discretely sampled intensity levels of each of the multiple light sources.

In various exemplary embodiments of the systems and methods according to this invention, an actual object to be viewed using the vision system is placed within the overall field of view of the vision system. Depending on the desired analysis to be made, either the entire object, or a specific portion of the object including a region of interest, is illuminated using an illumination setting including at least one of the various illumination sources of the vision system. A plurality of actual images of the object, or of the particular portion of the object, are captured, where each captured image is illuminated using a different illumination intensity of at least one such illumination source. This is repeated as necessary for the different illumination sources provided in the vision system. In various exemplary embodiments of the systems and methods according to this invention, each illumination source is used and varied independently of other sources, in the above process.

A simulation is performed to determine the effects of the multiple lighting sources on the object, or on the particular portion of the object, using any combination of the various lighting sources and using any combination of output intensities of the lighting sources. In order to direct the simulation toward the desired end, a user defines or selects a particular desired metric that is relevant to the analysis to be performed on the captured image of the object, or the portion of the object. The user also defines the specific portion of the image data of the captured image of the object, or the desired portion of the object, to be used. A combination of the multiple lighting sources is selected for simulation, as is a particular driving intensity for each of the lighting sources. If, for any selected lighting source, that lighting source is driven at a level that does not exactly correspond to one of the captured images for that lighting source, the intensity of that lighting source at the selected driving value is interpolated between the two or more of the actual values.

The resulting interpolated simulated images are then summed, on a pixel-by-pixel basis, to determine the net light intensity received from the object by the image capture device if the actual object were to be actually illuminated using the various selected lighting sources driven at the selected driving values. The resulting pixels of the simulated image that correspond to the pixels selected for analysis can then be evaluated to determine if the selected lighting sources and the selected drive values for those lighting sources result in the desired quality of illumination of the actual part, were that part actually illuminated, at the selected drive values, using the selected lighting sources.

For example, in various exemplary embodiments, the user can define, as the metric, to maximize the largest peak gradient in the scan line of interest. Another image characteristic metric can be to maximize the height of an edge peak while minimizing overall variation, i.e., texture, along a scan line. Depending on the metric chosen, various different search methods can be used during or following the simulation, ranging from simple to more complex methods. Furthermore, the search can be enhanced based on prior knowledge, i.e., the part being opaque and blocking the stage light.

In contrast to the previously discussed conventional methods, in various exemplary embodiments of the systems and methods according to this invention, slow hardware trial-and-error procedures are reduced, minimized or avoided completely. The previously known methods acquired an extensive image series to create final synthetic image. This final synthetic image is likely to be no better than the best previous image in the series in a particular sub-region of interest, and which is of dubious value for precise quantitative feature analysis. In contrast to these conventional methods, the systems and methods according to this invention acquire a relatively limited set of images, to rapidly determine hardware settings usable to acquire a final real image. These hardware settings may be selected for precise quantitative feature analysis in a particular sub-region of interest of the final real image.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

Figure 1:
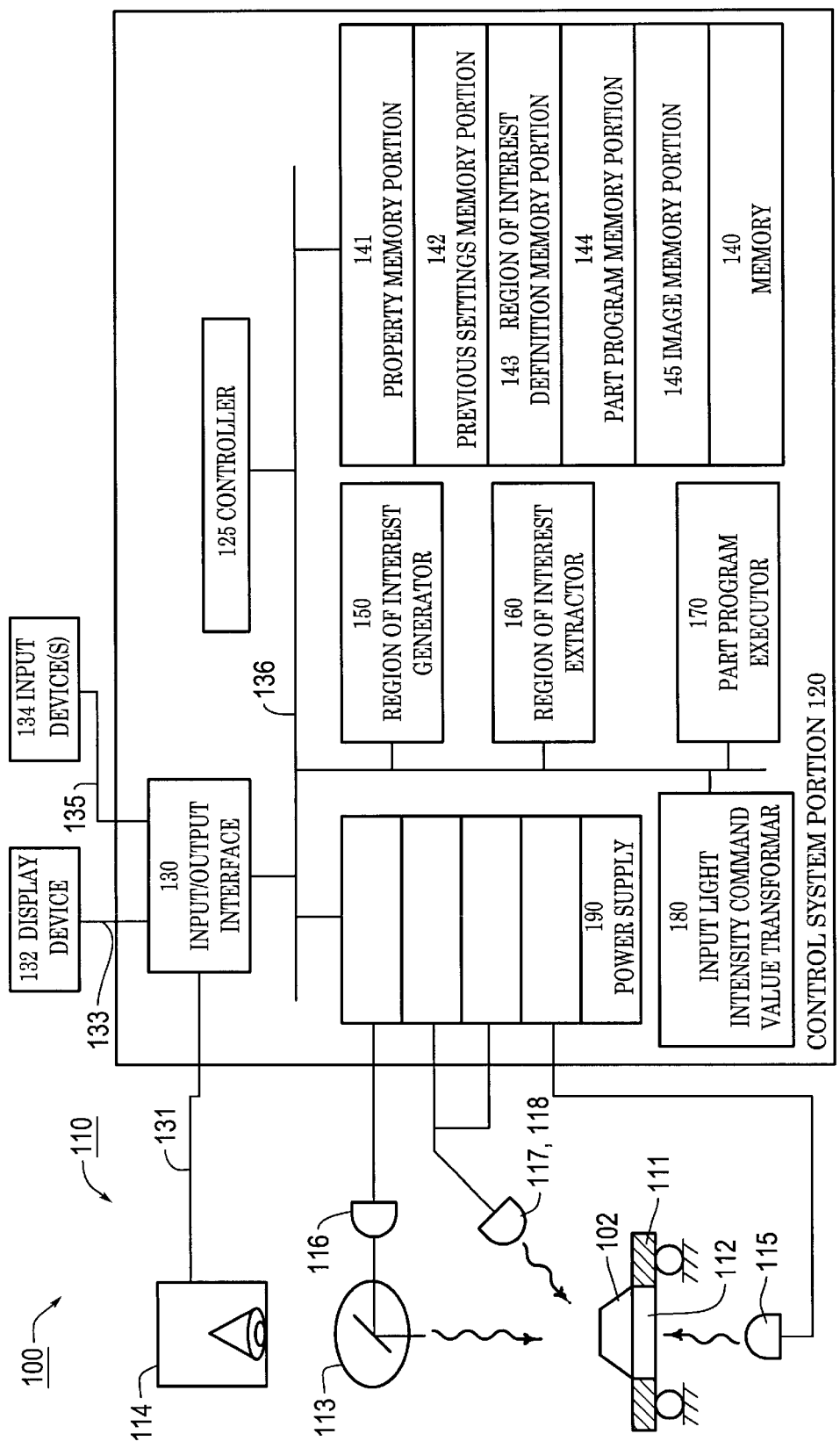
FIG. 1 a block diagram of one exemplary embodiment of a vision system having a light intensity control system according to this invention.

For simplicity and clarification, the operating principles, and design factors of various exemplary embodiments of the systems and methods according to this invention are explained with reference to one exemplary embodiment of a vision system 100, as shown in FIG. 1. The basic explanation of the operation of the vision system shown in FIG. 1 is applicable for the understanding and design of any vision system that incorporates this invention. Although the systems and methods of this invention are described in conjunction with this specific vision system 100, the systems and methods according to this invention can be used with any other known or later-developed vision system.

FIG. 1 shows a vision system 100. As shown in FIG. 1, the vision system 100 includes a vision system components portion 110 and a control portion 120. The control portion 120 includes elements, including a property memory portion 141 described below, which constitute a light intensity control system usable in accordance with this invention. The control portion 120 further includes elements, including a part program executor and/or generator 170 described below, which constitute a control instruction generation system usable in accordance with this invention.

The vision system components portion 110 includes a stage 111 having a central transparent portion 112. A part 102 to be imaged using the vision system 100 is placed on the stage 111. The light from a number of different light sources 115–118 passes through a lens system 113 after illuminating the part 102, and possibly before illuminating the part 102, and is gathered by a camera system 114 to generate an image of the part 102. The light sources used to illuminate the part 102 include a stage light 115, a coaxial light 116, and/or a surface light, such as a ring light 117 or a programmable ring light 118.

Each of the lights sources 115–118, separately, or in combination, constitute a controllable lighting system. It should be appreciated that any one of the various light sources 115–118 described above can include a plurality of different colored light sources. That is, for example, the stage light 115 can include a red light source, a green light source and a blue light source. Each of the red, blue and green light sources of the stage light 115 will be separately driven by the power source 190, and may be considered as a separate source in various embodiments of the systems and methods according to this invention.

It should also be appreciated that, if a focusable light source or a movable light source is included in the controllable lighting system, then, in various alternative exemplary embodiments of the systems and methods according to this invention, various discrete positions of the focusing element or discrete positions of the movable light source may be treated as separate light sources, in order to identify the most desirable lighting focus, or movable light position. It should be appreciated that any combination of known or later developed single-color, multi-color, fixed, moveable and/or focusable light sources may be used in conjunction with this invention without departing from the spirit and scope of the invention.

In general, all of the previously described controllable aspects of the various light sources included in the controllable lighting system are described by, and/or governed by an illumination setting. The illumination setting describes and/or determines the particular illumination configuration which is used to capture an associated image. In various exemplary embodiments, the illuminating setting may be represented as a lighting vector.

The image captured by the camera is output on a signal line 131 to the control portion 120. As shown in FIG. 1, the control portion 120 includes a controller 125, an input/output interface 130, a memory 140, a part program executor and/or generator 170, an input light intensity command value transformer 180, and a power supply 190, each interconnected either by a data/control bus 136 or by direct connections between the various elements. The signal line 131 from the camera system 114 is connected to the input/output interface 130. Also connected to the input/output interface 130 can be a display 132 connected over a signal line 133 and one or more input devices 134 connected over one or more signal lines 135. The display 132 and the one or more input devices 134 can be used to view, create and modify part programs, to view the images captured by the camera system 114 and/or to directly control the vision system components 110. However, it should be appreciated that, in a fully automated system having a predefined part program, the display 132 and/or the one or more input devices 134, and the corresponding signal lines 133 and/or 135 may be omitted.

Figure 3:
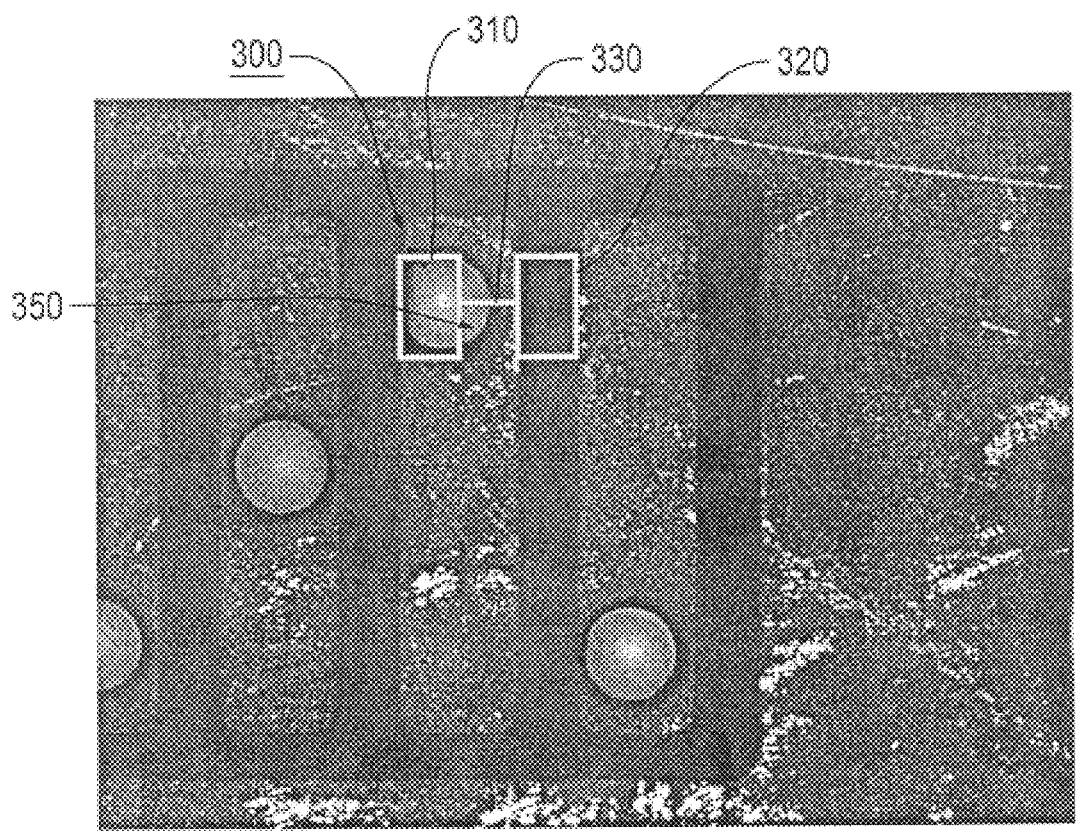
FIG. 3 illustrates an exemplary image and one exemplary embodiment of an image quality tool usable in conjunction with various embodiments of the systems and methods according to this invention.

As part of the memory 140, the part program memory portion 144 stores one or more part programs used to control the operation of the vision system 100 for particular types of parts. The image memory portion 145 stores images captured using the camera system 114 when operating the vision system 100. Furthermore, a region of interest definition memory portion 143 contains data defining the location of the region of interest within the captured region, including the parameters of a measurement tool, such as the image quality tool 300 shown in FIG. 3. The image quality tool 300 of FIG. 3 is described in greater detail below.

In the vision system 100, a previous setting memory portion 142 stores previous settings for the various light sources 115–118 that were in place prior to the part program executor and/or generator 170 adjusting one or more of the light sources 115–118. A property memory portion 141 stores data identifying the light source or sources that will be adjusted to obtain the desired image quality, data defining the operation mode for operating the various light sources 115–118, data defining the image quality that is to be used as the metric for determining whether the identified light source(s) to be used to illuminate the part 102 need further adjusting, and data defining whether the image data in the regions of interest is to be filtered.

It should be appreciated that the foregoing description of the vision system 100 used with this invention generally describes an automatic program operation. However, the vision system 100 used with this invention may also operate substantially the same when the illumination commands are issued manually through one or more input devices 134 during manual or stepwise operation of the vision system 100. Furthermore, although the vision system 100 is capable of adapting various parameters, this following discussion assumes that the configuration of the imaging system and the workpiece under inspection is already known or predictable. In addition, any focus conditions are assumed to have been met, and position and orientation of the lighting sources are fixed relative to the object or part 102.

When a machine vision system programmer wishes to illuminate a specific workpiece mounted on the stage 111, such as the part 102, to capture an image of that part, where the captured image has one or more specific image characteristics, the programmer would operate the vision system 100 to create a part program and typically select and define a number of specific image measurement or analysis tools which govern particular image analysis tasks. One exemplary image analysis tool, described for purposes of illustration herein, is the image quality tool 300 shown in FIG. 3, described in greater detail below.

More generally, when a measurement tool is set up by the operator during part programming, the scan line or area of the captured image used to determine the required measured value is defined in the tool. In particular, the part program will cause the vision system 100 to manipulate the stage 111 and/or the camera system 114 such that a particular portion of the part 102 is within the field of view of the camera system 114 and at a desired focus state. The part program executor and/or generator 170 would then, under the control of the controller 125, command the camera system 114 to capture an image of the part 102 and output the captured image to the control system 120. The control system 120 will then, under the control of the controller 125, input the captured image through the input/output interface 130 and store the captured image in the captured image storage portion 145 of the memory 140. The controller 125 will then display the captured image on the display device 132.

Figure 2:
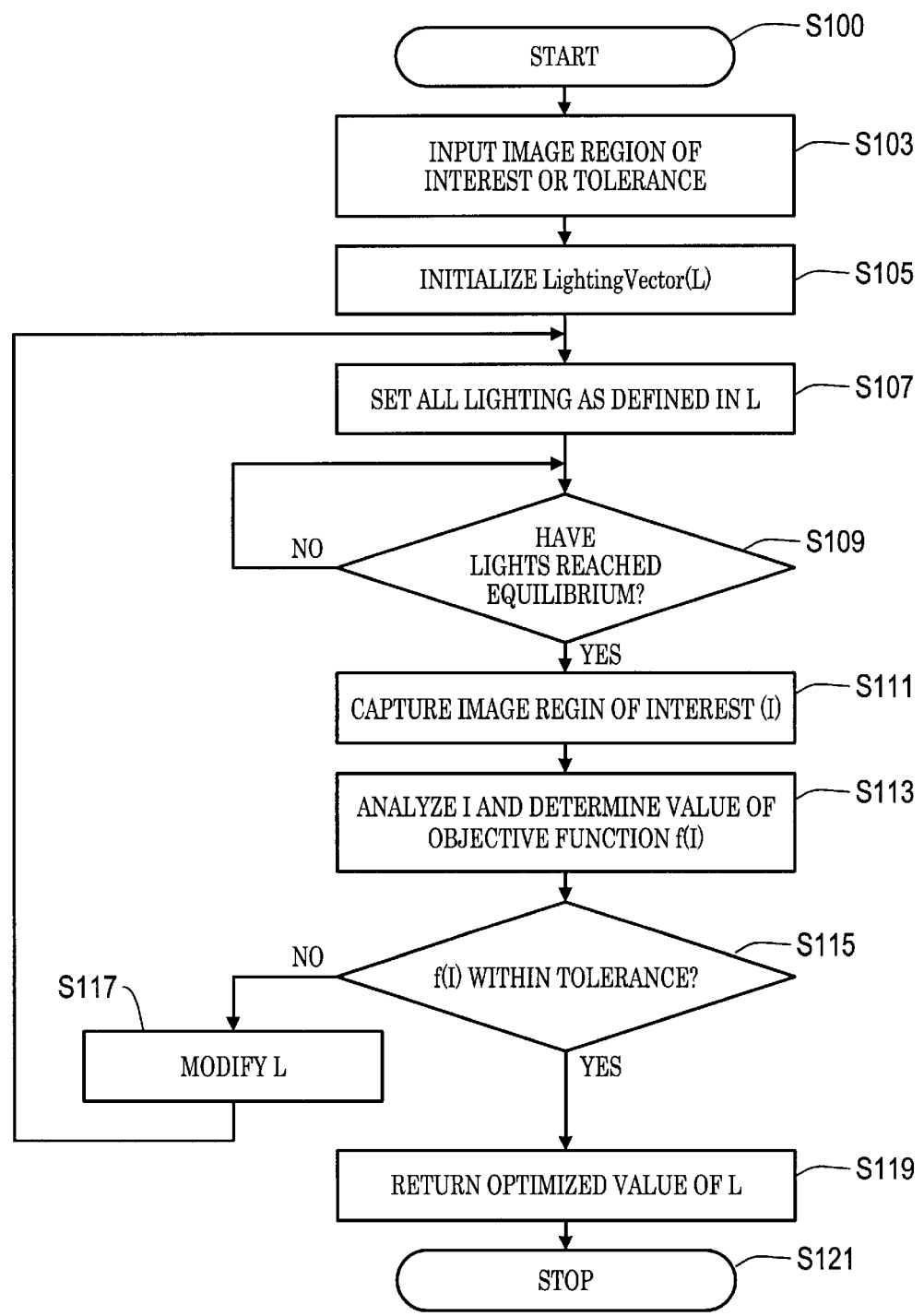
FIG. 2 is a flowchart outlining a conventional method for determining multi-channel lighting settings.

In order to determine the one or more lighting conditions that allow an image of the part 102 to be captured such that the captured image has the one or more desired image characteristics using the part program in the vision system 100, it is conventional to systematically vary the lighting conditions until the desired image characteristics are obtained. FIG. 2 is a flowchart outlining a conventional method for determining multi-channel lighting settings that allow an image having the desired image characteristics to be captured. In this conventional method, actual video data is analyzed for each set of lighting settings.

After beginning the method in step S100, control continues to step S103, where an image region of interest and/or an image characteristic tolerance value is defined. A tolerance value would indicate the range of image quality values that are acceptable and thus require no further adjustment of the lighting settings of the selected one or more light sources. Next, in step S105, a lighting vector L, i.e., the set of lighting settings for the one or more light sources, is initialized. The lighting vector L contains one entry for each light source, and each entry corresponds to the lighting power output by that light source. As previously discussed, various color sources within a light source, or other separately positioned and controllable sources within a light source, may be regarded as separate light sources. Then, in step S107, the lighting power outputs of the light sources of the vision system 100 are set to the level defined in the lighting vector L. Control then continues to step S109.

In step S109, a determination is made whether the light sources have reached a steady state. This is done, for example, with halogen light sources, which require a period of time to stabilize their illumination power output after their drive current is altered. If, in step S109, the lights have not reached a steady state, control jumps back to step S109 until all of the lights have reached a steady state. Once all of the light sources have reached steady state, control continues to step S111, where an image containing the image region of interest I is captured. Then, in step S113, the region of interest I is analyzed to determine a value of an objective function $f(I)$. In various exemplary embodiments, the resulting value is a scalar output. Next, in step S115, a determination is made whether or not the objective function $f(I)$ is within the selected, or alternatively within a predetermined, tolerance. If the objective function $f(I)$ is within the selected or predetermined tolerance, control jumps to step S119. Otherwise control continues to step S117, where the lighting vector L is modified.

In contrast, in step S119, the current lighting vector L is returned as a lighting vector that is able to illuminate the part 102 such that an image having the desired image characteristics can be captured. Then, in step S121, the method ends.

Figure 4:
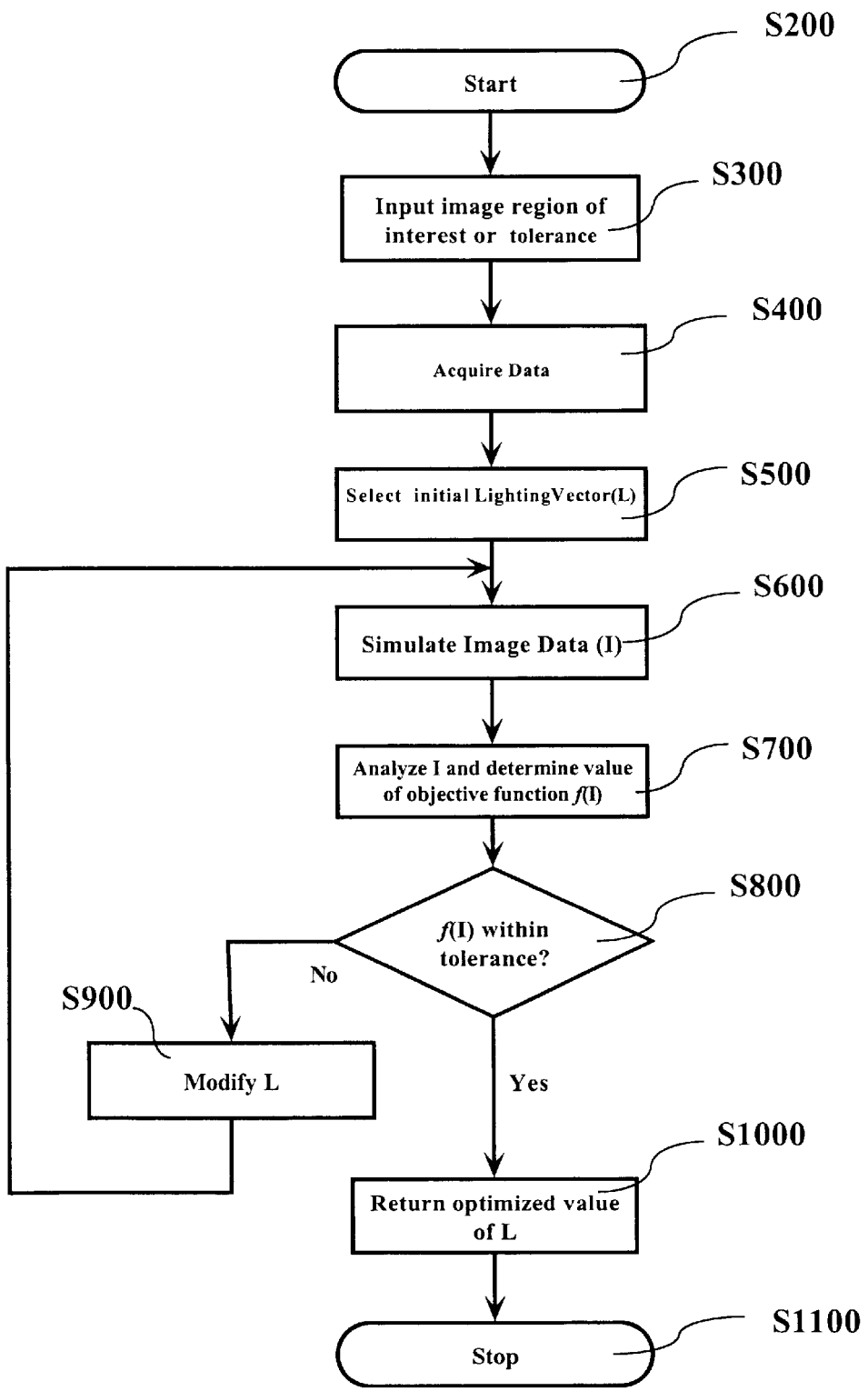
FIG. 4 is a flowchart outlining a first exemplary embodiment of a method for determining multi-channel lighting settings according to this invention.

In contrast to the foregoing conventional method based on hardware control adjustments and actual image acquisition, in the systems and methods according to this invention, the one or more lighting conditions that allow the part 102 to be captured with one or more desired image characteristics are determined by varying the lighting conditions in a virtual simulation, and analyzing the simulated video data. FIG. 4 is a flowchart outlining a first exemplary embodiment of a method according to this invention that uses simulated video data to determine the multi-channel lighting settings that allow an image having desired image characteristics to be captured.

After beginning in step S200, control continues to step S300, where the image region of interest and/or the image characteristic tolerance value is defined. Next, in step S400, a number of base images are acquired, where, in various exemplary embodiments, each base image is generated by illuminating the part 102 using a single one of the various light sources that is driven at one of a number of discrete power levels. Control then continues to step S500.

In step S500, a lighting vector L for the simulated image is initialized. In general, the lighting vector L contains one entry corresponding to each controllable aspect of each included light source. In general, the lighting vector L contains at least one entry corresponding to the lighting power output by each included light source. As previously discussed, various color sources, or other separately positioned and controllable sources, within a light source, as well as various discrete positions, or focus configurations, of a positionable or focusable light source, may be regarded as separate light sources. Control then continues to step S600.

In step S600, a simulated image having one or more of the light sources illuminating the part 102 is created for at least the region of interest, based on combining various ones of the acquired base images based on the current lighting vector L. Next, in step S700, the region of interest I of the simulated image is analyzed to determine a value of an objective function $f(I)$. Then, in step S800, a determination is made whether the objective function $f(I)$ is within the selected or predetermined tolerance. If the objective function $f(I)$ is not within the selected or predetermined tolerance, control continues to step S900. Otherwise, control jumps to step S1000.

In step S900, the lighting vector L is modified. Control then returns to step S600. In contrast, in step S1000, once the objective function $f(I)$ is within the selected or predetermined tolerance, the current lighting vector L is returned as a lighting vector that is able to illuminate the part 102 such that an image having the desired image characteristics can be captured. Then, in step S1100, the method ends.

It should appreciated that a simulated image can have a variety data representations. Furthermore, various evaluations which determine whether a desired image characteristic is achieved for a particular image, or simulated image, may require only part of the data conventionally expected to constitute a simulated image, or only particular metrics extracted from that data.

Various exemplary embodiments of the systems and methods according to this invention are described herein as generating a simulated image as the image result which is evaluated. In various other exemplary embodiments, however, the image result may be in a variety of forms not generally recognized as a simulated image. For example, depending on the desired image characteristic to be achieved, an objective function, or another form of image result, may be computed directly from the base images and a lighting vector without needing to represent or generate a simulated image. Provided that such image results are usable to determine whether a particular illumination setting achieves a desired image characteristic, such image results are included in the scope of the term "generates a simulated image" and are otherwise within the scope of the systems and methods according to this invention.

Figure 5:
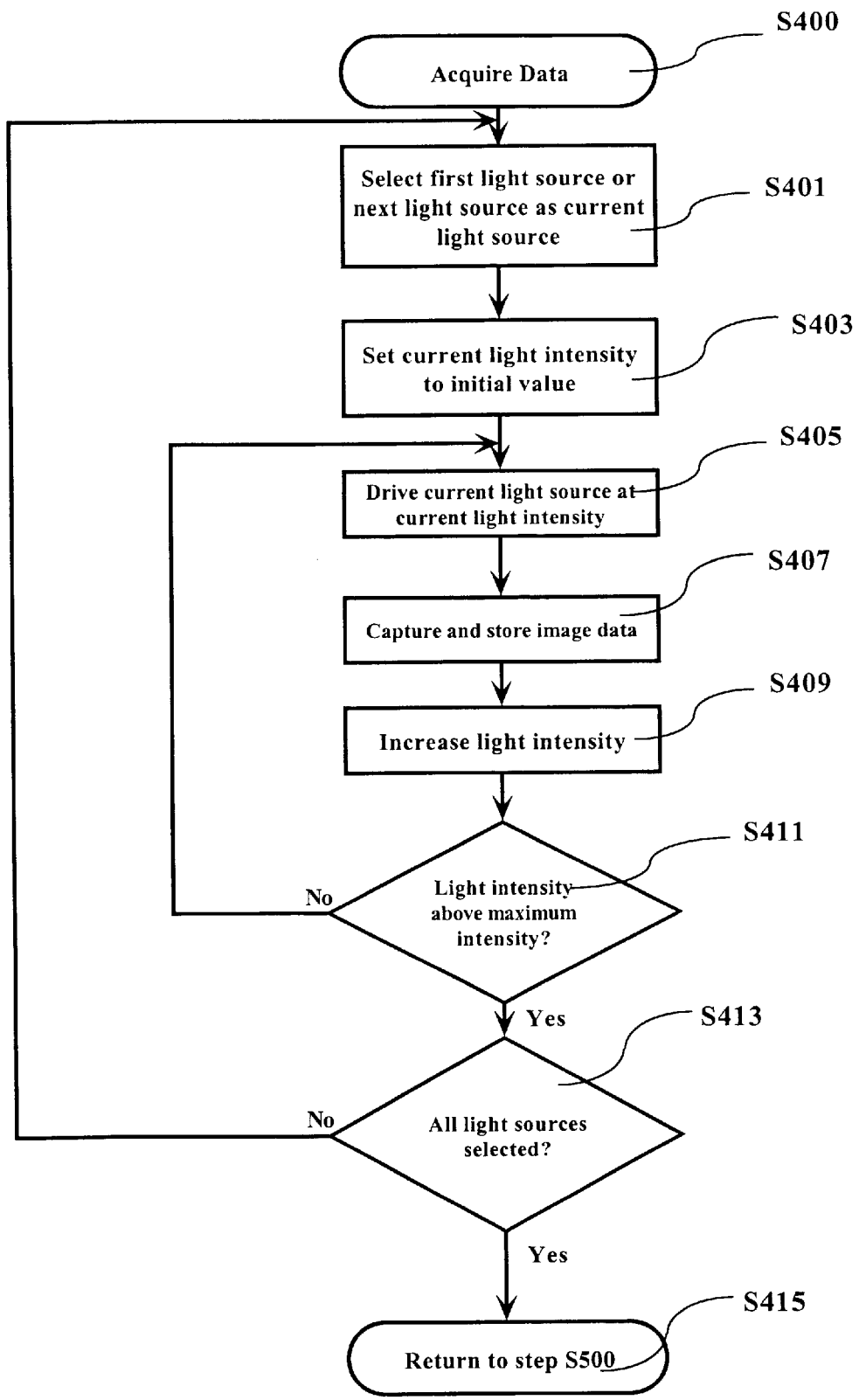
FIG. 5 is a flowchart outlining in greater detail one exemplary embodiment of the method for acquiring data of the actual object to be viewed using the determined lighting settings according to this invention.

FIG. 5 is a flowchart outlining in greater detail one exemplary embodiment of the method for acquiring data as described in FIG. 4. Beginning in step S400, control continues to step S401, where the total number of lighting sources being characterized is set to the number of different light sources that the user wishes to use to illuminate the part 102, or, alternatively, to a default condition defined according to the vision system lighting configuration, and a first or next one of light sources to be measured is selected as the current light source. Next, in step S403, a current light intensity value is set to a predetermined initial value. For example, the initial light intensity value can be set to zero percent. Then, in step S405, the current light source is driven to obtain the light output intensity designated by the current light intensity value. Control then continues to step S407.

In step S407, an image of the part 102 containing the image region of interest I, illuminated using the current light source and current light intensity value, is captured and stored in memory. Then, in step S409, the light output intensity value is increased by a predetermined or selected light intensity increment.

Next, in step S411, a determination is made whether the light output intensity value for the current light source is greater than a selected or predetermined level. If the light source output intensity value for the current light source is not greater that the selected or predetermined level, then control jumps back to step S405. Otherwise, if the light output intensity value for the current light source is greater than the selected or predetermined level, control continues to steps S413. In various embodiments, the inventors have determined that eight discrete light output intensity values provide a sufficient characterization for most light sources and that three or fewer discrete light output intensity values provide a sufficient characterization for certain light sources under certain operating conditions and/or certain assumptions based on knowledge of the light source behavior. In step S413, a determination is made whether all of the light sources have been selected as the current light source. If all of the light sources have not been selected, then control returns to step S403. Otherwise, control continues to step S415, where control returns to step S500.

When determining the additive effects of each source, the light sources can be assumed not to modify the reflectivity function of the part 102. Also, any image acquisition defects, such as, for example, blooming and the like, can be ignored. Under these conditions, the light measured at a pixel may be described as:

$$I(x, y) = R_{workpiece}(x, y) \times L_{coax}(x, y) + R_{workpiece}(x, y) \times L_{stage}(x, y) + R_{workpiece}(x, y) \times L_{ring}(x, y) \quad (1)$$

where:

I (x, y) is the image value of a pixel (x, y) in the simulated image;

R (x, y) is the scalar reflectivity of the material corresponding to the pixel at the coordinates (x, y); and $L_n$ (x, y) is the contribution of the $n^{th}$ light source to the material location corresponding to image coordinate (x, y).

Eq. (1) demonstrates that a video scan line created by any combination of the light sources can be realistically predicted. Thus, the simulated video scan line can be sufficient to determine one or more lighting conditions that allow an image of a part to be captured using multiple light sources, such that the captured image has the one or more desired image characteristics. The inventors have verified that this procedure can be used to determine the light settings for real images of regions of interest, and that the resulting images support precise quantitative analysis of the features and characteristics of a variety of objects.

Figure 6:
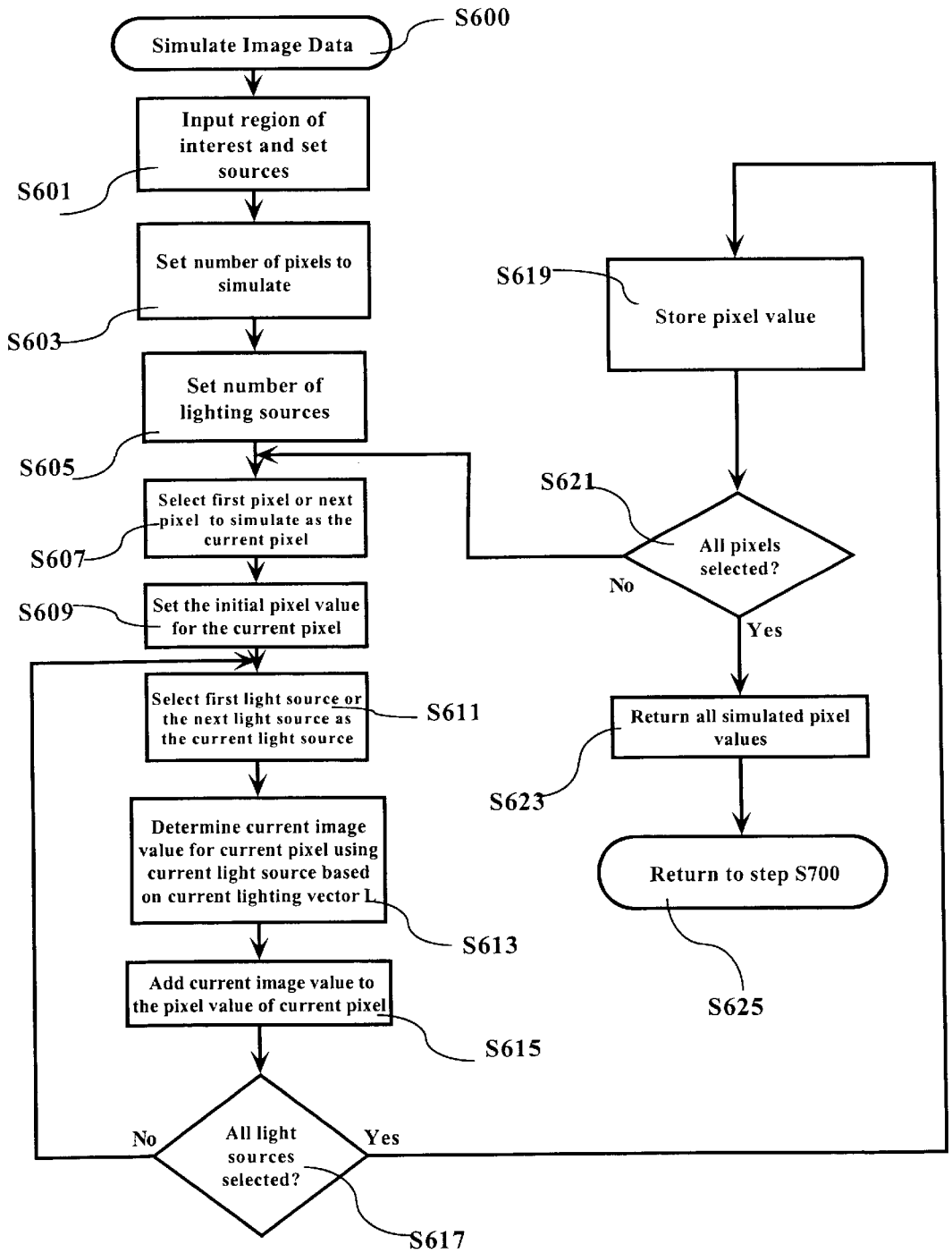
FIG. 6 is a flowchart outlining in greater detail one exemplary embodiment of the method for simulating image data according to this invention.

FIG. 6 is a flowchart outlining in greater detail one exemplary embodiment of the method of creating the simulated image, from one or more of the light sources illuminating the part 102, as described in FIG. 4. Beginning in step S600, control continues to step S601, where the region of interest, a listing of sources and the current lighting vector L for each lighting source, is identified or defined. Next, in step S603, the total number of pixels that the user wishes to simulate is identified or determined. Then, in step S605, the total number of lighting sources being combined is set to the number of different light sources that the user wishes to use, or, alternatively, to a default condition defined according to the vision system lighting configuration, or to an otherwise prescribed set of light sources. Control then continues to step S607.

In step S607, the first or next pixel to be simulated is selected as the current pixel. Then, in step S609, an initial pixel image value is set for the current pixel to be simulated. Next, in step S611, the first or next light source is selected as the current light source of the set of light sources listed in step S601. Control then continues to step S613.

In step S613, a current image value is determined for the current pixel to be simulated, for the current light source when driven based on the current lighting vector L. In particular, in various exemplary embodiments, if the current lighting vector L indicates a light intensity for the current light source that corresponds exactly to that of one of the previously-acquired base images, then the image value for the current pixel is equal to the image value for that pixel in that corresponding acquired base image. In contrast, in various exemplary embodiments, if the current lighting vector L value for the current light source does not exactly correspond to that of one of the previously-acquired base images, one or more of the previously-acquired base images having intensity values that lie on each side of the light intensity value for the current light source defined in the current lighting vector L are selected. Then, the image value for the current pixel is determined by interpolating between the image value for the corresponding pixels in the selected previously-acquired base images for the current pixel based on the light intensities of these previously-acquired base images and the light intensity of the current light source defined in the current lighting vector.

Of course, it should be appreciated that, rather than using just the immediately adjacent previously-acquired base images, any combination of one or more of the previously-acquired base images can be used to determine the image value for the current pixel when the light intensity for the current light source, defined in the current lighting vector L, does not exactly correspond to the light intensities for any of the previously-acquired base images. It should further be appreciated that, in various exemplary embodiments, the image value for a corresponding pixel in a previously-acquired base image can be used without change, as a reasonable approximation, even though the light intensity for that base image does not exactly correspond to the light intensity for the current lighting source defined in the current lighting vector L. This is particularly useful if the two light intensities are within a certain predetermined or selected range. Thus, it should be appreciated that other known or later-developed variations for determining the image value of the current pixel, when the current light source is driven at the light intensity defined in the current lighting vector L, can be used to determine the current image value of the current pixel from one or more of the acquired base images.

Then, in step S615, the current image value determined in step S613 is added to the pixel value for the current pixel. Next, in step S617, a determination is made whether all of the designated light sources have been selected for the current pixel. If all of the light sources for the current pixel have not been selected, control returns to step S611. Otherwise, control continues to step S619.

In step S619, the pixel value for the current pixel is stored as the simulated value for the current pixel. Next, in step S621, a determination is made whether all of the pixels to be simulated have been selected. If all of the pixels have not been selected, control returns to step S607. Otherwise, in step S623, all simulated pixel values are returned to represent an image that would be obtained if the part 102 were to be illuminated using the current lighting vector characteristics. Then, in step S625, the method ends.

Returning now to a discussion of FIG. 3, FIG. 3 illustrates an exemplary image and one exemplary embodiment of an image quality tool 300 usable in conjunction with various embodiments of the systems and methods according to this invention. In particular, the exemplary image quality tool 300 shown in FIG. 3 is a dual area image quality tool, as described in greater detail in U.S. application Ser. No. 09/484,897, incorporated herein by reference in its entirety. As shown in FIG. 3, the dual area image quality tool 300 includes a first region of interest 310 and a second region of interest 320 connected by a bar 330.

As described in the incorporated 897 application, a user can manually operate a vision machine in training mode. In this training mode the user can manipulate the dual area image quality tool 300 to ensure that the regions of interest 310 and 320 include the proper portions of the captured image and/or to ensure that the bar 330 extends across a critical feature to be measured, such as the edge 350. Once the user is satisfied that the dual area image quality tool 300 is properly positioned, the user establishes a target value for the dual area image quality tool 300. This target value is established, for example, by adjusting the light sources until the user's subjective evaluation of the image quality in the critical region is favorable.

The user then signals the control system 100 to incorporate the current tool parameters into the part program. In response, the part program generator and/or executor 170 generates a part program instruction based on the current state of the dual area image quality tool 300. Then, one or more values corresponding to the image quality or characteristic are determined from the current, subjectively-favored image data. That value then that becomes the stored numerical target reference value that governs the run-time lighting adjustments during future automatic execution of the part program.

However, it should be appreciated that various exemplary embodiments of the systems and methods according to this invention can be used in conjunction with the dual area image quality tools as described in the incorporated 897 application. For example, various embodiments of the systems and methods according to this invention can be used to replace or assist the user during any or all of the operations that adjust the light sources, evaluate when the image quality in the critical region is favorable, establish the target value for the dual area image quality tool 300, and/or signal the control system 100 to incorporate the current tool parameters into the part program.

Thus, it should be appreciated that various exemplary embodiments of the systems and methods according to this invention can be used to enhance and/or automate not only the dual area image quality tool 300, but a wide variety of other known and/or later-developed image analysis tools, regardless of their apparent operating limitations and/or manual nature in the absence of the systems and methods according to this invention.

Further, it should be appreciated that the potential of various exemplary embodiments of the systems and methods according to this invention for automatic operation, and relatively high-speed execution, allows the systems and methods according to this invention to be implemented at run time, to check and/or adjust for unforeseen conditions such as unexpected ambient lighting conditions, lighting system faults, and process-drift or the like, if appropriate. Such applications of the various exemplary embodiments of the systems and methods according to this invention therefore allow an unprecedented level of reliability and robustness to be achieved, particularly with precision automatic vision systems.

Figure 7:
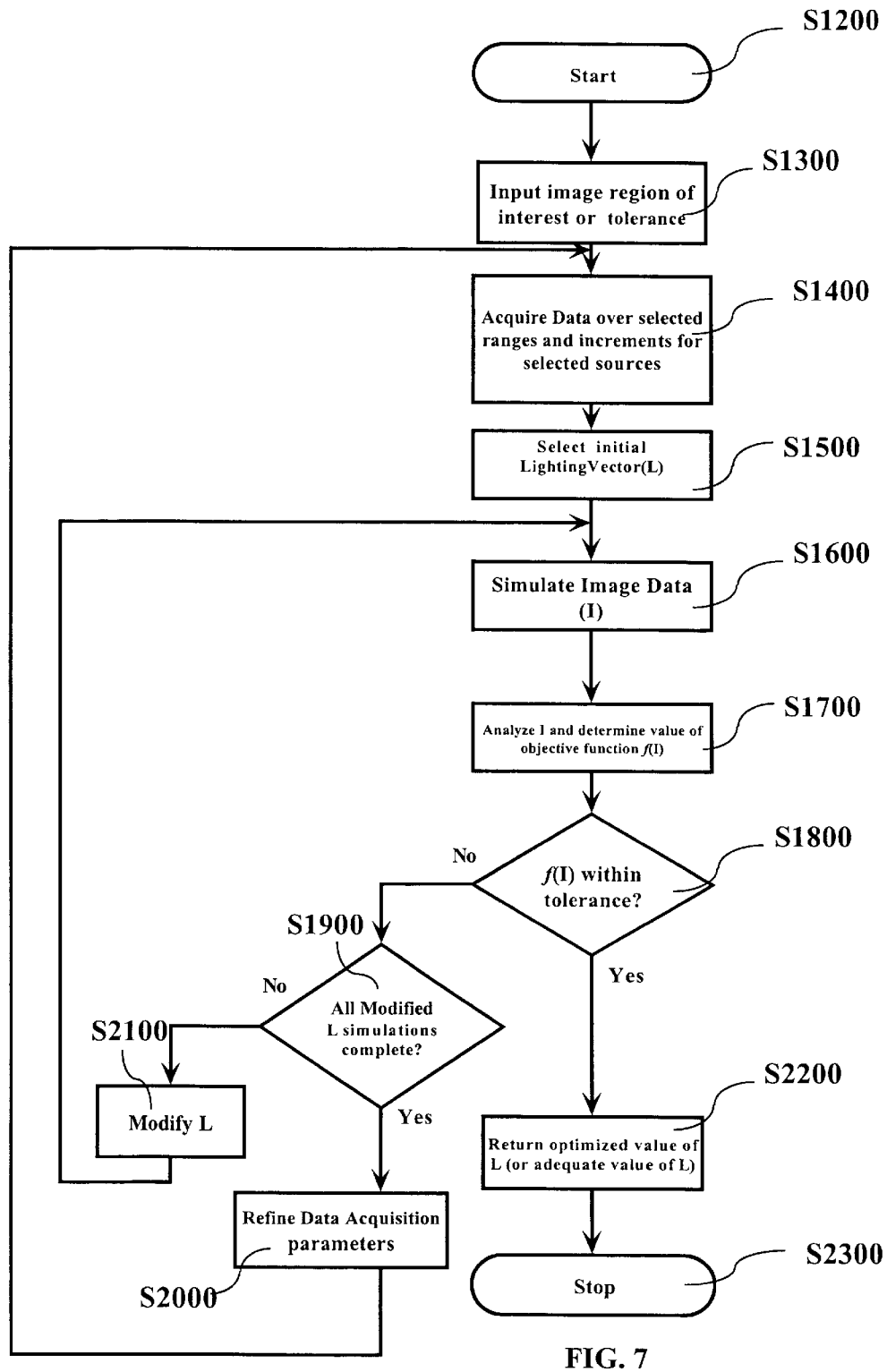
FIG. 7 is a flowchart outlining a second exemplary embodiment of a method for determining multi-channel lighting settings according to this invention.

FIG. 7 is a flowchart outlining a second exemplary embodiment of a method according to this invention that uses simulated video data to determine the multi-channel lighting settings that allow an image having desired image characteristics to be captured. The exemplary embodiment outlined in FIG. 7 generally corresponds to the exemplary embodiment outlined in FIG. 4, and the various embodiments outlined in FIGS. 5 and 6 are generally usable in conjunction with the exemplary embodiment outlined in FIG. 7, and described below. However, the exemplary embodiment outlined in FIG. 7 illustrates further advantages of speed and flexibility that may be achieved according to various exemplary embodiments of the systems and methods according to this invention.

The exemplary embodiment outlined in FIG. 7 is particularly suitable, for example, to implement an iterative coarse-fine search technique to reduce one of the most time-consuming steps of the overall procedure, the actual hardware data acquisition, to a practical minimum. As the execution time of the overall procedure is reduced, various exemplary embodiments of the systems and methods of this invention gain significantly wider utility and advantage, particularly with regard to automatic operation and run-time applications.

As outlined in FIG. 7, after beginning in step S1200, control continues to step S1300, where the image region of interest and/or the image characteristic tolerance value is defined. Next, in step S1400, a number of base images are acquired.

In this exemplary embodiment, based on previous experience with the vision machine and/or class of object to imaged, the light sources and/or the light source drive ranges are selected to be restricted to those sources and drive ranges which most often produce desirable image results. Thereafter, each base image is generated by illuminating the part 102 using a single one of the various selected light sources. The selected light source is initially driven over the selected range, at one of a limited number of coarsely-spaced discrete power levels within the selected range. In contrast to conventional methods, this approach is feasible because the simulation-based systems and method according to this invention can be executed sufficiently rapidly that there is little penalty if the acquired data fails to include support for simulation of the settings which satisfy the requirements for the objective function. In such as case, as further described below, additional base image data can be acquired as needed, without significant delay. Control then continues to step S1500.

In step S1500, a lighting vector L for the simulated image is initialized. The lighting vector L contains one entry for each of the previously selected light sources to be used in generating the simulated image, and each entry corresponds to the simulated lighting power output by that light source to determine the simulated image. Then, in step S1600, a simulated image having one or more of the previously selected light sources illuminating the part 102 is created for at least the region of interest, based on combining various ones of the acquired base images based on the current lighting vector L, as previously described in various embodiments herein. Next, in step S1700, the region of interest I of the simulated image is analyzed to determine a value of an objective function $f(I)$. Control then continues to step S1800.

In step S1800, a determination is made whether the objective function $f(I)$ is within the selected or predetermined tolerance. If the objective function $f(I)$ is not within the selected or predetermined tolerance, control continues to step S1900. Otherwise, control jumps to step S2200.

In step S1900, a determination is made whether the lighting vector L has undergone all modifications which are expected to be simulated for the present iteration of simulations, according to the particular coarse-fine search strategy implemented. If all the expected modifications of L have been simulated, then the present iteration of the coarse-fine search strategy has failed. As a result, control continues step S2000. Otherwise, control jumps to step S2100.

In step S2000, the coarse-fine search strategy is carried to the next level, by refining the data acquisition parameters to provide additional base images. The additional base images may be provided by parameters corresponding to additional light sources, expanded drive ranges, and/or more finely spaced discrete power levels within the drive ranges, according to the particular search strategy implemented. In a least efficient scenario according to various exemplary embodiments, the data acquisition parameters may be set to acquire data according to the first exemplary embodiment outlined in FIG. 4. Control then returns to step S1400.

In contrast, in step S2100, the lighting vector L is modified. It should be noted that, in various exemplary embodiments, the lighting vector L is not modified according to a coarse-fine search strategy, but is systematically modified. This is done because the associated simulation process typically executes so rapidly that there is little practical gain to be realized from a coarse-fine search strategy for the light vector L. However, in various other exemplary embodiments, a coarse-fine search strategy for the light vector L is easily implemented by methods well-known to those skilled the art. Control then returns to step S1600.

As indicated above, once the determination in step S1800 shows that the objective function $f(I)$ is within the selected or predetermined tolerance, control continues to step S2200. In step S2200, the current lighting vector L is returned as a lighting vector that is able to illuminate the part 102 such that an image having the desired image characteristics can be captured. Then, in step S2300, the method ends.

It should be appreciated that, in various other exemplary embodiments, this second exemplary embodiment of the systems and methods according to this invention may be designed for faster execution speed. In this case, the returned lighting vector may not be fully optimized among all available alternatives, but may simply be adequate according to the requirements set for the objective function. It should be further appreciated, that in the foregoing exemplary embodiments, the base images are acquired using single light sources.

However, it should be appreciated that Eq. (1) implies that it is alternatively possible to acquire a set base images using a plurality of light sources for each such base image. Each such base image may then be decomposed to identify the contributions of each light source by appropriate analysis of the set of images. Therefore, it should be appreciated that such an alternative exemplary embodiments lie within the scope of this invention.

In FIG. 1, the control system portion 120 is, in various exemplary embodiments, implemented using a programmed general purpose computer. However, the control system portion 120 can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowcharts shown in FIGS. 4–6 can be used to implement the control system portion 120.

In FIG. 1, alterable portions of the memory 140 are, in various exemplary embodiments, implemented using static or dynamic RAM. However, the memory 140 can also be implemented using a floppy disk and disk drive, a writeable optical disk and disk drive, a hard drive, flash memory or the like. In FIG. 1, the generally static portions of the memory 140 are, in various exemplary embodiments, implemented using ROM. However, the static portions can also be implemented using other non-volatile memory, such as PROM, EPROM, EEPROM, an optical ROM disk, such as a CD-ROM or DVD-ROM, and disk drive, flash memory or other alterable memory, as indicated above, or the like.

Thus, in FIG. 1, the memory 140 can be implemented using any appropriate combination of alterable, volatile or non-volatile memory or non-alterable, or fixed, memory. The alterable memory, whether volatile or non-volatile, can be implemented using any one or more of static or dynamic RAM, a floppy disk and disk drive, a writeable or re-rewriteable optical disk and disk drive, a hard drive, flash memory or the like. Similarly, the non-alterable or fixed memory can be implemented using any one or more of ROM, PROM, EPROM, EEPROM, an optical ROM disk, such as a CD-ROM or DVD-ROM disk, and disk drive or the like.

It should also be understood that each of the circuits of the control system portion 120 shown in FIG. 1 can be implemented as portions of a suitably programmed general purpose computer. Alternatively, each of the circuits shown in the control system portion 120 of FIG. 1 can be implemented as physically distinct hardware circuits within an ASIC, or using a FPGA, a PDL, a PLA or a PAL, or using discrete logic elements or discrete circuit elements. The particular form each of the circuits shown in the control system portion 120 of FIG. 1 will take is a design choice and will be obvious and predictable to those skilled in the art.

Moreover, the control system portion 120 can be implemented as software executing on a programmed general purpose computer, a special purpose computer, a microprocessor or the like. In this case, the control system portion 120 can be implemented as a routine embedded in the vision system 100, as a resource residing on a server, or the like. The control system portion 120 can also be implemented by physically incorporating it into a software and/or hardware system.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A vision system comprising:
   a controllable lighting system;
   an imaging system; and
   a light intensity control system, wherein:
      the light intensity control system is operable to determine a prescribed illumination setting usable to achieve a desired image characteristic in a region of interest to be imaged by the vision system, the prescribed illumination setting determined based on a plurality of actual images corresponding to actual illumination settings; and
      wherein the prescribed illumination setting is determined based on evaluating at least one combination of at least two of the plurality of actual images, and at least one combination of at least two of the plurality of actual images comprises a simulated image.

2. The vision system of claim 1, wherein the at least one combination of at least two of the plurality of actual images comprises an interpolated image obtained by interpolating between the image values of corresponding pixels included in the at least two of the plurality of actual images.

3. The vision system of claim 2, wherein the at least one combination of at least two of the plurality of actual images comprises a simulated image.

4. The vision system of claim 3, wherein:
   the prospective illumination setting comprises a lighting vector; and
   the prescribed illumination setting comprises a lighting vector selected based on an evaluation of the at least one combination of at least two of the plurality of actual images.

5. The vision system of claim 4, wherein the evaluation of the at least one combination of at least two of the plurality of actual images comprises an analysis of the at least one combination of at least two of the plurality of actual images that indicates whether the combination achieves the desired image characteristic in the region of interest.

6. The vision system of claim 1, wherein each of the plurality of actual images corresponding to actual illumination settings comprises at least the region of interest.

7. The vision system of claim 1, wherein the controllable lighting system is controlled based on the prescribed illumination setting.

8. The vision system of claim 1, wherein the prescribed illumination setting is used when acquiring an image including at least the region of interest.

9. The vision system of claim 1, wherein the light intensity control system is operable by at least one of manual control of the vision system by a user, and automatic control of the vision system under the instructions of a program.

10. The vision system of claim 9, wherein the light intensity control system is operable to determine at least one prescribed illumination setting during automatic control of the vision system under the instructions of a program.

11. The vision system of claim 10, wherein the at least one prescribed illumination setting determined during automatic control of the vision system under the instructions of a program is used to at least one of control the controllable lighting system and compare a current illumination setting to a comparable previously-determined illumination setting.

12. The vision system of claim 1, wherein:
   the light intensity control system is part of a general computerized control system of the vision system, the general computerized control system further comprising a control instruction generation system;
   the light intensity control system is operable by the control instruction generation system; and
   the control instruction generation system generates at least one of a part program, an inspection program control instruction, and a controllable lighting system control instruction based on a prescribed illumination setting determined by the light intensity control system.

13. The vision system of claim 12, wherein:
   the control instruction generation system includes at least one image analysis tool; and
   at least one of a desired image characteristic and a desired region of interest is defined according to at least one characteristic of an associated one of the at least one image analysis tool.

14. The vision system of claim 1, wherein the controllable lighting system comprises at least two of a stage light, a coaxial light, a ring light and a programmable ring light.

15. The vision system of claim 1, wherein the controllable lighting system comprises a plurality of differently colored light emitting elements of a single light device.

16. A method for determining a prescribed illumination setting for a vision system having a controllable lighting system, the prescribed illumination setting usable to acquire a desired image, that has a desired image characteristic in a region of interest, the method comprising:
   obtaining a plurality of base images of at least the region of interest, each base image comprising an actual image corresponding to an actual illumination setting;
   determining, for at least the region of interest, a simulated image result based on a current prospective illumination setting and at least one of the base images;
   evaluating whether the simulated image result corresponds to a desired image;
   modifying the current prospective illumination setting at least if the simulated image result does not correspond to the desired image; and
   repeating the determining, evaluating and modifying steps until at least one simulated image result corresponds to the desired image.

17. The method of claim 16, wherein:
   the controllable lighting system comprises a plurality of light sources; and
   obtaining the plurality of base images of at least the region of interest comprises:
      selecting one of the plurality of light sources; and
      driving the selected light source at at least one selected light intensity value, each selected light intensity value corresponding to a respective base image.

18. The method of claim 17, wherein driving the selected light source at at least one selected light intensity value comprises driving the selected light source at a plurality of discrete light intensity values in a selected range.

19. The method of claim 18, wherein the plurality of discrete light intensity values in a selected range comprises less than 8 discrete light intensity values.

20. The method of claim 18, wherein obtaining the plurality of base images comprises selecting each of at least two of the plurality of light sources.

21. The method of claim 18, wherein each current prospective illumination setting comprises a lighting vector, the lighting vector comprising at least a light intensity value for each light source included in the lighting vector.

22. The method of claim 21, wherein:

the simulated image result is determined for a selected plurality of pixels to be simulated; and determining the simulated image result comprises:

identifying a current one of the plurality of pixels to be simulated, selecting at least one base image corresponding to illumination by a current light source included in the lighting vector, determining an image value to combine into the total image value for the current pixel based on the selected at least one base image corresponding to illumination by the current light source and the light intensity value for the current light source in the lighting vector, combining the image value into a total simulated image value for the current pixel, and repeating the identifying, selecting, determining, and combining steps such that the total image value for each of the selected plurality of pixels to be simulated includes the combined image values of at least the light sources included in the lighting vector which have a non-zero light intensity value.

23. The method of claim 22, wherein:

the selected at least one base image comprises at least two base images corresponding respectively to at least two discrete light intensity values for the current light source; and determining the image value to combine into the total image value for the current pixel comprises determining the image value to combine into the total image value for the current pixel by one of interpolation and extrapolation, based on the image values for the current pixel in the selected bases images, the light intensity values for the current light source in the selected base images, and the light intensity value of the current light source in the current lighting vector.

24. The method of claim 16, wherein:

the method comprises a number of iterations;

obtaining the plurality of base images comprises obtaining a first plurality of base images during a first iteration and at least one additional base image during each subsequent iteration;

the current prospective illumination setting comprises one of a current series of illumination settings corresponding to a current iteration; and repeating at least the determining, evaluating and modifying steps until at least one simulated image result corresponds to a desired image comprises:

repeating the determining, evaluating and modifying steps corresponding to the current iteration until one of:

at least one simulated image result corresponds to a desired image, or a simulated image result has been evaluated for each illumination setting in the current series and no evaluated simulated image result corresponds to a desired image, and performing, if no evaluated simulated image result corresponds to a desired image, a subsequent iteration comprising the obtaining, determining, evaluating, modifying and repeating steps, until at least one simulated image result corresponds to a desired image.

25. The method of claim 16, wherein:

modifying the current prospective illumination setting at least if the simulated image result does not correspond to a desired image comprises modifying the current prospective illumination setting only if the simulated image result does not correspond to a desired image comprises; and the current prospective illumination setting corresponding to the one simulated image result that corresponds to a desired image is the prescribed illumination setting.

26. The method of claim 16, wherein:

modifying the current prospective illumination setting at least if the simulated image result does not correspond to a desired image comprises modifying the current prospective illumination setting if one of:

the simulated image result does not correspond to a desired image comprises or until a simulated image result has been evaluated for each prospective illumination setting in a prescribed series of prospective illumination settings; and choosing, if more than one prospective illumination setting corresponding to a desired image is identified, the prescribed illumination setting to be the prospective illumination setting corresponding to the best result for the desired image characteristic.

27. The method of claim 16, further comprising controlling the controllable lighting system based on the prescribed illumination setting to acquire the desired image.

28. The method of claim 16, wherein the desired image characteristic comprises at least one of a contrast, a brightness, and a gradient value corresponding to an edge feature included in at the region of interest.

29. A recording medium that stores a control program, the control program executable on a computing device, the computing device couplable to a vision system, the control program including instructions for determining a prescribed illumination setting for a vision system having a controllable lighting system, the prescribed illumination setting usable to acquire a desired image that has a desired image characteristic in a region of interest, the instructions comprising:

instructions for obtaining a plurality of base images of at least the region of interest, each base image comprising an actual image corresponding to an actual illumination setting;

instructions for determining, for at least the region of interest, a simulated image result based on a current prospective illumination setting and at least one of the base images;

instructions for evaluating whether the simulated image result corresponds to the desired image;

instructions for modifying the current prospective illumination setting at least if the simulated image result does not correspond to the desired image; and instructions for repeating the determining, evaluating and modifying instructions until at least one simulated image result corresponds to a desired image.

30. A carrier wave encoded to transmit a control program to a device for executing the control program, the device couplable to a vision system, the control program including instructions for determining a prescribed illumination setting for a vision system having a controllable lighting system, the prescribed illumination setting usable to acquire a desired image, that has a desired image characteristic in a region of interest, the instructions comprising:

instructions for obtaining a plurality of base images of at least the region of interest, each base image comprising an actual image corresponding to an actual illumination setting;

instructions for determining, for at least the region of interest, a simulated image result based on a current prospective illumination setting and at least one of the base images;

instructions for evaluating whether the simulated image result corresponds to the desired image;

instructions for modifying the current prospective illumination setting if the simulated image result does not correspond to the desired image; and instructions for repeating at least the determining, evaluating and modifying steps until at least one simulated image result corresponds to the desired image.

* * * * *